US00PP22441P2

(12) United States Plant Patent
Haba

(10) Patent No.: US PP22,441 P2
(45) Date of Patent: Jan. 3, 2012

(54) ***PETUNIA* PLANT NAMED 'KIRIMAJI DOUBLE RED'**

(50) Latin Name: *Petunia×hybrida*
Varietal Denomination: Kirimaji Double Red

(75) Inventor: Kiyoto Haba, Yokohama (JP)

(73) Assignee: Japan Agribio Company, Tokyo (JP)

( * ) Notice: Subject to any disclaimer, the term of this patent is extended or adjusted under 35 U.S.C. 154(b) by 0 days.

(21) Appl. No.: 12/924,153

(22) Filed: Sep. 22, 2010

(51) Int. Cl.
*A01H 5/00* (2006.01)

(52) U.S. Cl. ..... Plt./356.23

(58) Field of Classification Search ..... Plt./356.23
See application file for complete search history.

*Primary Examiner* — Annette Para
(74) *Attorney, Agent, or Firm* — Audrey Charles

(57) ABSTRACT

A new and distinct cultivar of *Petunia* plant named 'Kirimaji Double Red', characterized by its double-type, medium red-colored flowers, medium green-colored foliage, and moderately vigorous, low mounded and spreading growth habit, is disclosed.

1 Drawing Sheet

Latin name of genus and species of plant claimed: *Petunia× hybrida.*

Variety denomination: 'Kirimaji Double Red'.

BACKGROUND OF THE INVENTION

The present invention relates to a new and distinct cultivar of *Petunia* plant botanically known as *Petunia×hybrida* and hereinafter referred to by the cultivar name 'Kirimaji Double Red'.

The new cultivar originated in a controlled breeding program in Japan Agribio Company Limited during April 2006. The objective of the breeding program was the development of *Petunia* cultivars with double type flowers, attractive flower coloration, and a strong, spreading growth habit.

The new *Petunia* cultivar is the result of cross-pollination. The female (seed) parent of the new cultivar is the proprietary *Petunia×hybrida* breeding selection designated PA 1-1-1, not patented, characterized by its single-type, medium red-colored flowers, medium green-colored foliage, and moderately vigorous, trailing growth habit. The male (pollen) parent of the new cultivar is the proprietary *Petunia×hybrida* breeding selection designated DW-Re, not patented, characterized by its double-type, medium red-colored flowers, medium green-colored foliage, and moderately vigorous, upright growth habit. The new cultivar was discovered and selected as a single flowering plant within the progeny of the above stated cross-pollination during May 2007 in a controlled environment at Japan Agribio Company Limited.

Asexual reproduction of the new cultivar by terminal stem cuttings since May 2007 at Japan Agribio Company Limited and West Chicago, Ill. has demonstrated that the new cultivar reproduces true to type with all of the characteristics, as herein described, firmly fixed and retained through successive generations of such asexual propagation.

SUMMARY OF THE INVENTION

The following characteristics of the new cultivar have been repeatedly observed and can be used to distinguish 'Kirimaji Double Red' as a new and distinct cultivar of *Petunia* plant:

1. Double-type, medium red-colored flowers;
2. Medium green-colored foliage; and 3. Moderately vigorous, low mounded and spreading growth habit.

Plants of the new cultivar differ from plants of the female parent primarily in flower type and growth habit and from plants of the male parent primarily in growth habit.

Of the many commercially available *Petunia* cultivars, the most similar in comparison to the new cultivar is SweetSunshine Red 'KLEH07144', not patented. However, in side by side comparisons, plants of the new cultivar differ from plants of 'KLEH07144' in at least the following characteristics:

1. Plants of the new cultivar have a flower petal color that is darker than plants of 'KLEH07144'; and
2. Plants of the new cultivar have smaller flowers, as measured by corolla diameter, than plants of 'KLEH07144'.

BRIEF DESCRIPTION OF, THE PHOTOGRAPHS

The accompanying photographs show, as nearly true as it is reasonably possible to make the same in color illustrations of this type, typical flower and foliage characteristics of the new cultivar. Colors in the photographs differ slightly from the color values cited in the detailed description, which accurately describes the colors of 'Kirimaji Double Red'. The plants were grown in 4-inch pots for 6 weeks in a greenhouse at West Chicago, Ill.

DETAILED BOTANICAL DESCRIPTION

Figure 1:
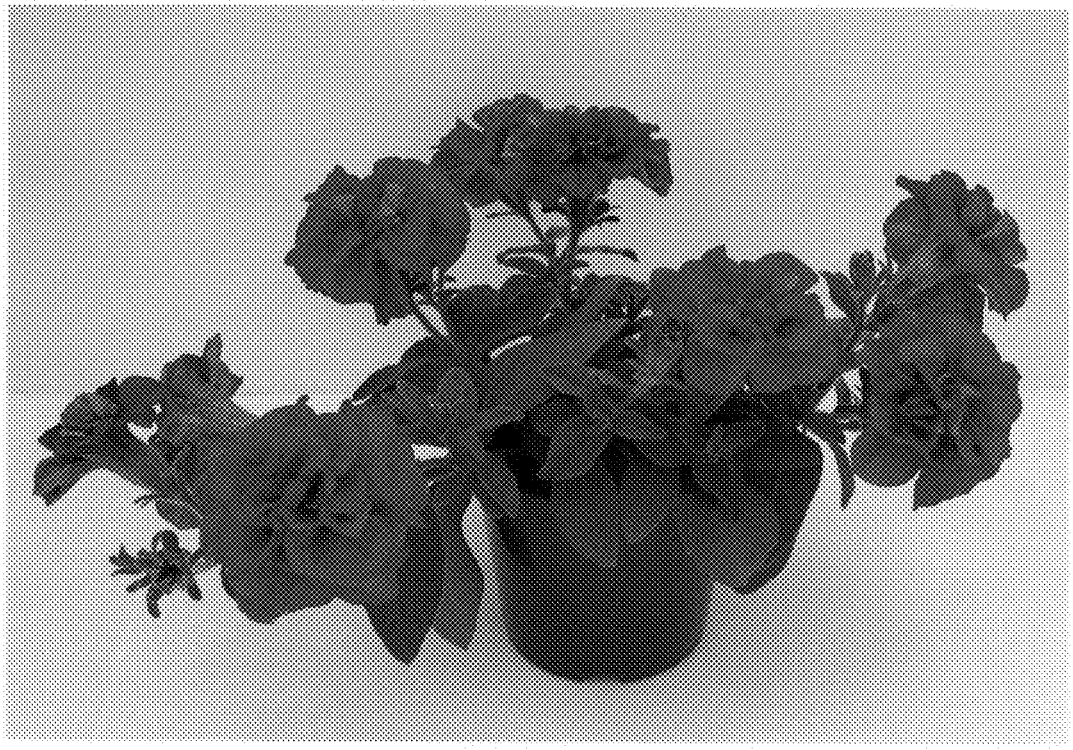
FIG. 1 illustrates a side view of the overall growth and flowering habit of 'Kirimaji Double Red'.
Figure 2:
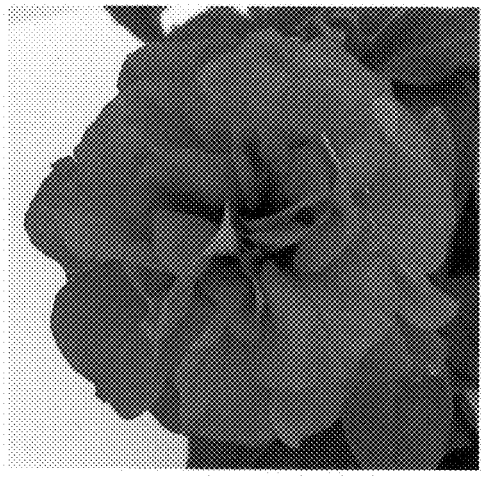
FIG. 2 illustrates a close-up view of an individual flower of 'Kirimaji Double Red'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2001 edition, except where general color terms of ordinary significance are used. The color values were determined in May 2010 under natural light conditions in West Chicago, Ill.

The following descriptions and measurements describe plants produced from cuttings from stock plants and grown in a glass-covered greenhouse under conditions comparable to those used in commercial practice. The plants were grown in West Chicago, Ill. in 4-inch pots for 6 weeks utilizing a soilless growth medium. Greenhouse temperatures were maintained at approximately 70° F. to 77° F. (21° C. to 25° C.) during the day and approximately 65° F. to 68° F. (18° C. to 20° C.) during the night. Greenhouse light levels of 2,500 footcandles to 6,000 footcandles were maintained during the day. Measurements and numerical values represent averages of typical plants.

Botanical classification: *Petunia×hybrida* cultivar Kirimaji Double Red.

Parentage:

*Female parent.*—Proprietary *Petunia×hybrida* breeding selection designated PA 1-1-1, not patented.

*Male parent.*—Proprietary *Petunia×hybrida* breeding selection designated DW-Re, not patented.

Propagation:

*Type cutting.*—Terminal stem.

*Time to initiate roots.*—Approximately 6 to 9 days.

*Time to produce a rooted cutting.*—Approximately 21 to 28 days.

*Root description.*—Fibrous.

*Rooting habit.*—Freely branching.

Plant description:

*Commercial crop time.*—Approximately 6 to 8 weeks from a rooted cutting to finish in a 10 cm pot.

*Growth habit and general appearance.*—Moderately vigorous, low mounded and spreading.

*Size.*—Height from soil level to top of plant plane: Approximately 11.3 cm. Width: Approximately 30.1 cm.

*Branching habit.*—Freely branching, pinching improves basal branching. Quantity of main branches per plant: Approximately 4.

*Branch.*—Strength: Strong. Length: Approximately 13.1 cm. Diameter: Approximately 5.0 cm. Length of central internode: Approximately 1.5 cm. Texture: Densely pubescent with a mixture of long and short glandular hairs. Color of young and mature stems: 144A.

Foliage description:

*General description.*—Quantity of leaves per main branch: Approximately 10. Fragrance: Slight. Form: Simple. Arrangement on flowering stem: Opposite.

*Leaves.*—Aspect: Right to obtuse angle to stem. Shape: Ovate. Margin: Entire. Apex: Acute. Base: Attenuate. Venation pattern: Pinnate. Length of mature leaf: Approximately 6.2 cm. Width of mature leaf: Approximately 3.4 cm. Texture of upper and lower surfaces: Densely pubescent with a mixture of long and short glandular hairs. Color of upper surface of young and mature foliage: 137A with venation of 146D. Color of lower surface of young and mature foliage: Closest to 146B with venation of 146D.

*Petiole.*—Length: Approximately 7.0 mm. Width: Approximately 4.0 mm. Texture: Densely pubescent with a mixture of long and short glandular hairs. Color: 146D.

Flowering description:

*Flowering habit.*—'Kirimaji Double Red' is freely flowering under outdoor growing conditions with substantially continuous blooming from spring through autumn and year-round in greenhouse environment.

*Lastingness of individual flower on the plant.*—Approximately 5 to 7 days.

Flower description:

*General description.*—Type: Double, solitary, funnel-form. Quantity per plant: Approximately 8. Fragrance: Slight, sweet.

*Bud.*—Rate of opening: Generally takes 2 to 3 days for bud to progress from first color to fully open flower. Quantity per plant: Approximately 2.

*Bud just before opening.*—Shape: Oblong. Length: Approximately 3.0 cm. Diameter at apex: Approximately 1.8 cm. Diameter at base: Approximately 3.0 mm. Texture: Densely glandular pubescent. Color of petals: 183D. Color of tube: 183C with venation of 145A.

*Corolla.*—Diameter: Approximately 5.8 cm. Depth: Approximately 5.2 cm.

*Petals.*—Quantity: 7 outer petals fused at base to form a tube; approximately 20 to 25 irregularly shaped petaloids arranged in 3 to 4 whorls. Shape: Roughly fan shaped to obovate. Appearance: Dull. Margin: Entire, wavy. Apex: Rounded. Length from tube: Approximately 2.3 cm. Length of free portion: Approximately 9.5 mm. Width: Approximately 2.7 cm. Texture of upper surface: Glabrous. Texture of lower surface: Sparsely pubescent. Color of upper surface when first open: 46B with midveins of 46A. Color of lower surface when first and fully open: Closest to 46D with midveins of 145A. Color of upper surface when fully open: Between 46B and 46C with midveins of 46A.

*Corolla tube.*—Length: Approximately 2.9 cm. Diameter at distal end: Approximately 1.7 cm. Diameter at proximal end: Approximately 3.0 mm. Texture of inner surface: Glabrous. Texture of outer surface: Densely glandular pubescent. Color of inner surface: 185D with venation of 183A. Color of outer surface: 186D with venation of 145A.

*Sepals.*—Quantity per flower: 5, fused at base. Shape: Linear. Apex: Obtuse. Length: Approximately 1.5 cm. Width: Approximately 4.0 mm. Texture of upper and lower surfaces: Densely pubescent with a mixture of long and short glandular hairs. Color of upper surface: 137B. Color of lower surface: 137C.

*Peduncle.*—Strength: Strong. Aspect: Acute angle to stem. Length: Approximately 2.3 cm. Diameter: Approximately 2.0 mm. Texture: Densely pubescent with a mixture of long and short glandular hairs. Color: 144A.

*Reproductive organs.*—None observed.

Seed and fruit production: Neither seed nor fruit production has been observed.

Disease and pest resistance: Resistance to pathogens and pests common to *Petunia* has not been observed.

What is claimed is::

1. A new and distinct cultivar of *Petunia* plant named 'Kirimaji Double Red', substantially as herein shown and described.

* * * * *